(12) United States Patent
Hsiao

(10) Patent No.: US 11,975,126 B2
(45) Date of Patent: May 7, 2024

(54) AROMA DIFFUSER USING A CASSETTE TYPE AROMA BOTTLE

(71) Applicant: DONGGUAN YIH TEH ELECTRIC PRODUCTS CO., LTD., DongGuan (CN)

(72) Inventor: Ming Jen Hsiao, Miaoli County (TW)

(73) Assignee: DONGGUAN YIH TEH ELECTRIC PRODUCTS CO., LTD., Dongguan (CN)

( * ) Notice: Subject to any disclaimer, the term of this patent is extended or adjusted under 35 U.S.C. 154(b) by 861 days.

(21) Appl. No.: 17/083,980

(22) Filed: Oct. 29, 2020

(65) Prior Publication Data

US 2021/0046208 A1 Feb. 18, 2021

Related U.S. Application Data

(63) Continuation-in-part of application No. 16/691,866, filed on Nov. 22, 2019, now Pat. No. 11,213,600, which is a continuation-in-part of application No. 16/162,374, filed on Oct. 16, 2018, now abandoned, which is a continuation-in-part of application No. 15/914,963, filed on Mar. 7, 2018, now abandoned.

(51) Int. Cl.
*A61L 9/03* (2006.01)

(52) U.S. Cl.
CPC ......... *A61L 9/037* (2013.01); *A61L 2209/133* (2013.01)

(58) Field of Classification Search
CPC ...... A61L 9/037; A61L 2209/133; A61L 9/03; A61L 2209/135
See application file for complete search history.

(56) References Cited

U.S. PATENT DOCUMENTS

| 5,192,009 | A | 3/1993 | Hidebrands |
| 5,711,674 | A | 1/1998 | Chu |
| 9,511,166 | B1 | 12/2016 | Li |
| 9,517,286 | B1 * | 12/2016 | Li ........................ B05B 7/2429 |
| 9,539,355 | B2 | 1/2017 | Hsiao |
| 9,849,206 | B1 | 12/2017 | Hsiao |
| 2007/0207066 | A1 | 9/2007 | Thur |
| 2013/0174842 | A1 * | 7/2013 | Young ............... A61M 16/1075 128/203.14 |
| 2014/0037273 | A1 * | 2/2014 | Jaworski ................. A61L 9/037 392/390 |
| 2014/0133131 | A1 | 5/2014 | Hsiao |
| 2014/0339337 | A1 | 11/2014 | Hsiao |
| 2018/0103507 | A1 * | 4/2018 | Davis ..................... A61L 9/032 |

* cited by examiner

*Primary Examiner* — Sean E Conley
*Assistant Examiner* — Brendan A Hensel
(74) *Attorney, Agent, or Firm* — Chun-Ming Shih; HDLS IPR SERVICES

(57) ABSTRACT

An aroma diffuser using a cassette type aroma bottle: includes a cassette type aroma bottle with a carrier having capillary pores for absorbing an aroma liquid, and a heater for heating the aroma liquid in the capillary pores of the carrier to dissipate the aromatic molecules into the outside air. When the aroma liquid is used up, the cassette type aroma bottle can be easily and rapidly detached for replacement. The aroma liquid absorbed by the carrier will not flow out of the carrier even if the cassette type aroma bottle is tilted or dumped during use or movement, ensuring safe use.

15 Claims, 15 Drawing Sheets

US 11,975,126 B2

AROMA DIFFUSER USING A CASSETTE TYPE AROMA BOTTLE

This application is a Continuation-in-Part of application Ser. No. 16/691,866, filed Nov. 22, 2019.

BACKGROUND OF THE INVENTION

1. Field of the Invention

The present invention relates to scent releasing devices and more specifically, to an aroma diffuser using a cassette type aroma bottle.

2. Description of the Related Art

Aroma diffusers have some problems of heating the aromatic fluid. For example, conventional aroma diffusers use an aroma bottle filled with an aroma liquid for dissipating aroma molecules. The aroma bottle is a glass bottle with an externally threaded bottleneck. In installation, the user needs to thread the externally threaded bottleneck of the aroma bottle upwardly into the inner thread at the bottom side of the aroma diffuser by one single hand. The user often has the disadvantage of not being able to thread the externally threaded bottleneck of the aroma bottle into the inner thread of the aroma diffuser accurately. So, the process of replacing the aroma bottle is slow and inconvenient. Furthermore, the structure of the inner thread of the aroma diffuser will wear quickly with use. If the structure of the inner thread of the aroma diffuser starts to wear, the aroma bottle will loosen up.

The aromas for aroma diffuser are mainly indoor fragrances that contain fragrance oils used in indoor spaces. Generally, many commercially available fragrance oils are not pure ingredients, and they all have certain essential oil carriers. Therefore, the use of these fragrances requires external factors to effectively emit fragrance in indoor spaces. For example, using an aroma heater to heat fragrances for producing good smell, which is different from the use of antiperspirant fragrance or perfume.

SUMMARY OF THE INVENTION

The present invention has been accomplished under the circumstances in view. It is therefore an object of the present invention to provide an aroma diffuser using a cassette type aroma bottle, which firmly secures the installed cassette type aroma bottle, effectively heats the aroma liquid in the cassette type aroma bottle to emit aroma molecules, and facilitates quick replacement of the cassette type aroma bottle when the aroma liquid is used up.

It is another object of the present invention to provide an aroma diffuser using a cassette type aroma bottle, which uses a carrier having capillary pores to absorb the aroma liquid from the cassette type aroma bottle. The carrier has a free end side extended out of the cassette type aroma bottle and accurately and positively protruding into a heat collection area of the heater without contacting the heater so that the aroma liquid absorbed by the carrier will not stick to the heater for heating. So, it can prevent the aroma liquid from sticking or adsorbing on the heater, thus avoiding the leakage of the aroma liquid from the heater to the internal of the aroma diffuser.

To achieve these and other objects of the present invention, an aroma diffuser using a cassette type aroma bottle: comprises a housing, a heater, an electric plug and a bottle holder. The housing is a hollow shell, comprising an opening, a first hole and a second hole. The opening is located on one lateral side of the housing. The second hole is located on the other lateral side of the housing opposite to the opening. The first hole is disposed perpendicularly between the opening and the second hole. The heater is mounted inside the housing. The electric plug is mounted in the first hole and electrically connected with the heater. The bottle holder is mounted in the second hole, comprising a plug hole defined therein, at least one guide groove respectively recessed from the periphery of the plug hole, and a bracket formed on an upper peripheral edge of the plug hole. The electric plug is used to connect to a power supply unit for providing electricity to the heater for generating heat. The heater can be a resistor, a thermistor, a cement resistor or a PTC (Positive Temperature Coefficient) supplemental heater.

The aroma diffuser using a cassette type aroma bottle: further comprises a cassette type aroma bottle. The cassette type aroma bottle comprises a bottle body, a carrier, a neck, a bottle opening, at least one locating block and an aroma liquid. The aroma liquid is filled in the bottle body. The neck is upwardly extended from an upper side of the bottle body. The bottle opening is formed in a top side of the neck. The locating blocks are respectively extended from the periphery of the neck. The carrier has one side thereof mounted in the bottle opening and disposed in contact with the aroma liquid, and an opposite side thereof extended out of the bottle opening. The internal capillary pores of the carrier absorb the aroma liquid. The aroma liquid is continuously absorbed by the capillary pores of the carrier and transferred to the part of the carrier outside the bottle opening. The aroma liquid residing inside the capillary pores of the carrier can contact the air to volatilize the aroma molecules. The cassette type aroma bottle can be assembled from the guide groove in the plug hole on the bottom side of the bottle holder conveniently and quickly by the locating block, whereby the cassette type aroma bottle is firmly connected to the aroma diffuser without loosening.

In some embodiments, the bracket comprises a position-limiting member with a position-limiting hole defined therein. The position-limiting member is disposed inside the bracket and spaced from an upper side of the circumference of the plug hole. The position-limiting hole is formed inside the position-limiting member corresponding to the plug hole.

Preferably, the heater further comprises a heat collection structure selectively formed of a hole in a middle part of the heater or a curved wall extended along one side of the heater with a heat collection area defined therein. The carrier has at least one part thereof surrounded by the heat collection structure.

The cassette type aroma bottle is mounted in the plug hole of the bottle holder of the aroma diffuser. The carrier outside the bottle opening is mounted in the position-limiting hole of the position-limiting member with the free end side of the carrier suspending in the hole or curved wall of the heat collection structure of the heater without touching the heater. Therefore, the aroma liquid will not stick to the heater and is prohibited from flowing over the inside of the aroma diffuser.

Preferably, the housing further comprises an annular flange extended from the border of the opening to a predetermined height, and a guide cup made in the form of a tube and fastened to the periphery of the annular flange. The guide cup can guide the volatile fragrance of the heated aroma liquid to the environment outside the aroma diffuser, and the guide cup has a decorative effect.

DETAILED DESCRIPTION OF THE PREFERRED EMBODIMENT

Figure 1:
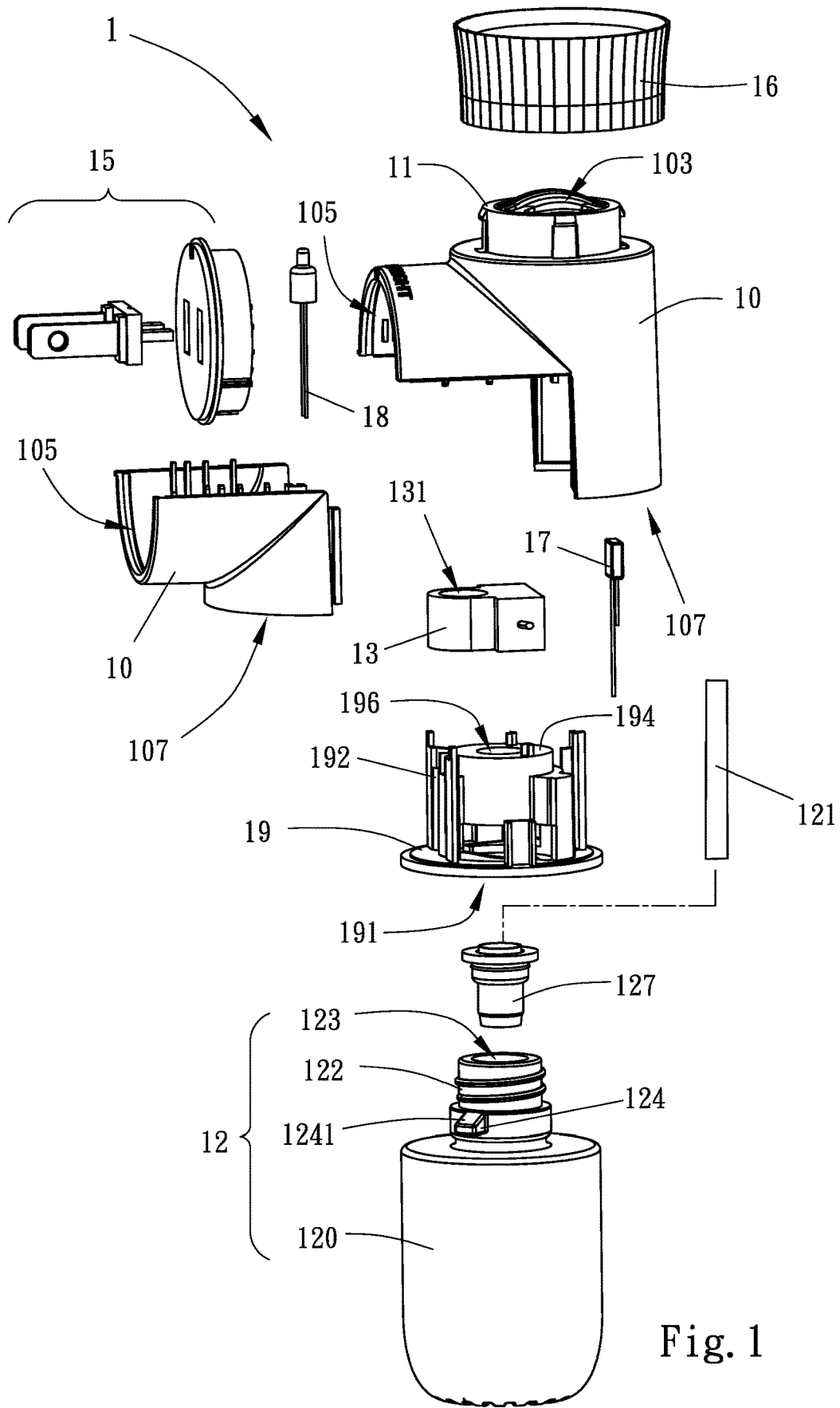
FIG. 1 is an exploded view of an aroma diffuser using a cassette type aroma bottle in accordance with the present invention.
Figure 2:
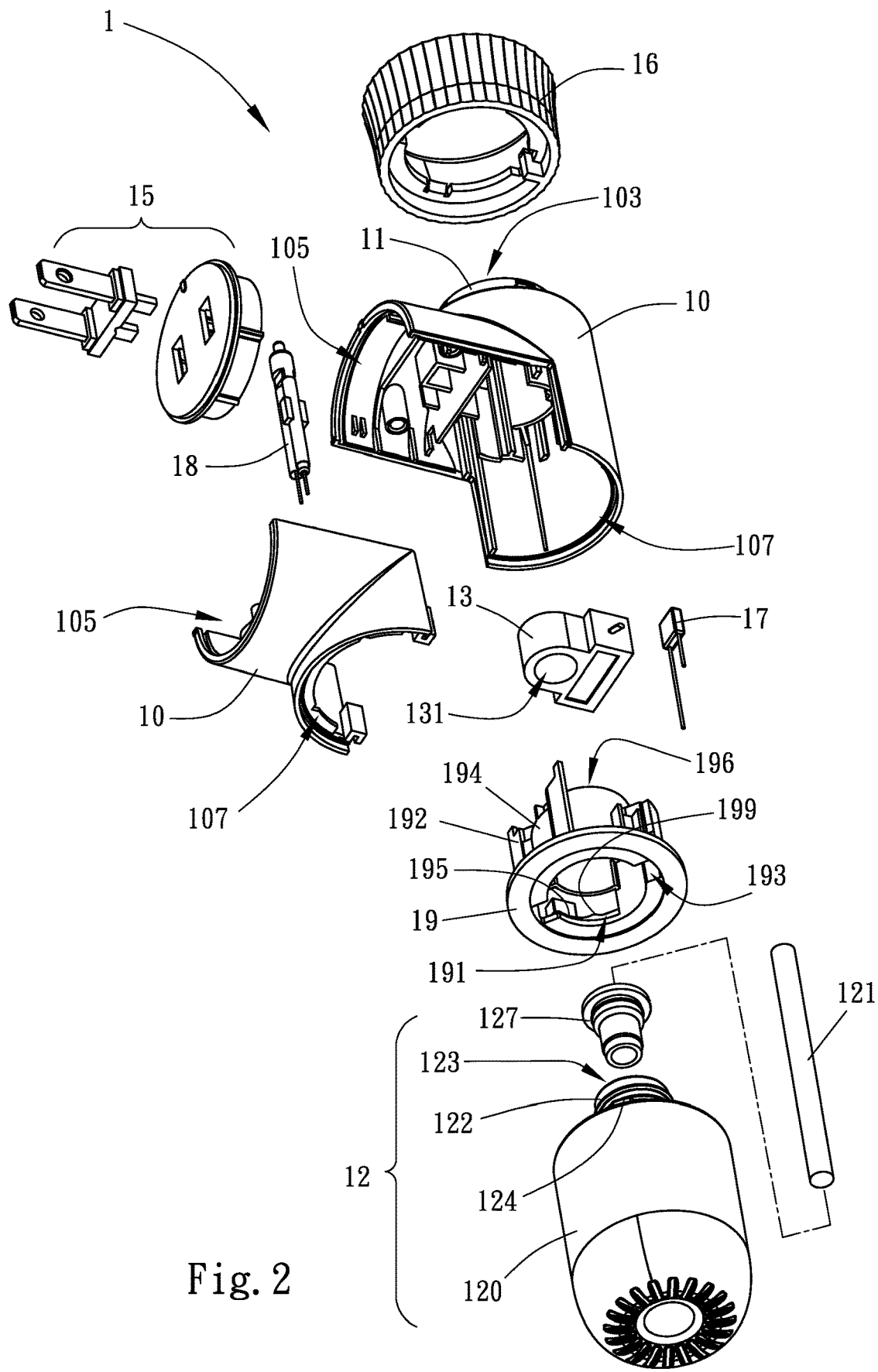
FIG. 2 is another exploded view of the aroma diffuser shown in FIG. 1.
Figure 3:
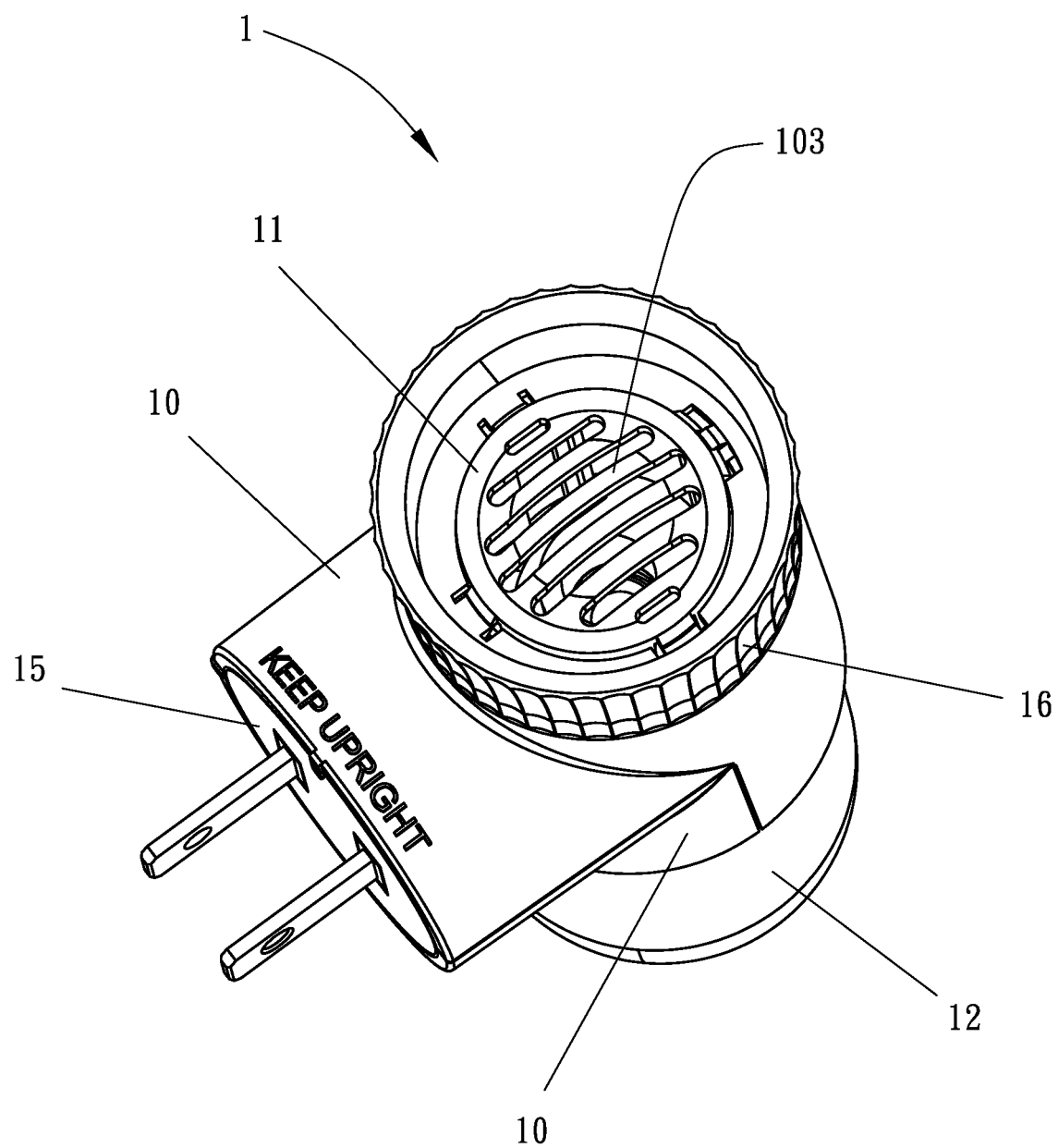
FIG. 3 is an oblique top elevation of the aroma diffuser shown in FIG. 1.

Referring to FIGS. 1-12, an aroma diffuser 1 using a cassette type aroma bottle in accordance with the present invention is shown. The aroma diffuser 1 using a cassette type aroma bottle comprises a housing 10, a heater 13, an electric plug 15, and a bottle holder 19.

The housing 10 is a hollow shell. The housing 10 has an opening 103, a first hole 105 and a second hole 107. The opening 103 is located on one side of the housing 10. The second hole 107 is located on an opposite side of the housing 10. The first hole 105 in this embodiment is perpendicularly disposed between the opening 103 and the second hole 107. The heater 13 is mounted inside the housing 10. The electric plug 15 is coupled to the first hole 105. The heater 13 is electrically connected to the electric plug 15. The bottle holder 19 is coupled to the second hole 107. The bottle holder 19 has a plug hole 191, a bracket 192, and at least one guide groove 193 located in the plug hole 191. The plug hole 191 is located on the bottom side of the bottle holder 19. The guide groove 193 is recessed from the side of the plug hole 191. In the present preferred embodiment, as illustrated in the annexed drawings, two guide grooves 193 are provided. The bracket 192 is disposed around the top side of the plug hole 191. The heater 13 can be combined with the bracket 192. The electric plug 15 is used to connect to a power supply unit (not shown) to provide power to the heater 13 for generating heat. The heater 13 is, for example, a resistor, a thermistor, a cement resistor or a PTC (Positive Temperature Coefficient) supplemental heater.

Figure 5:
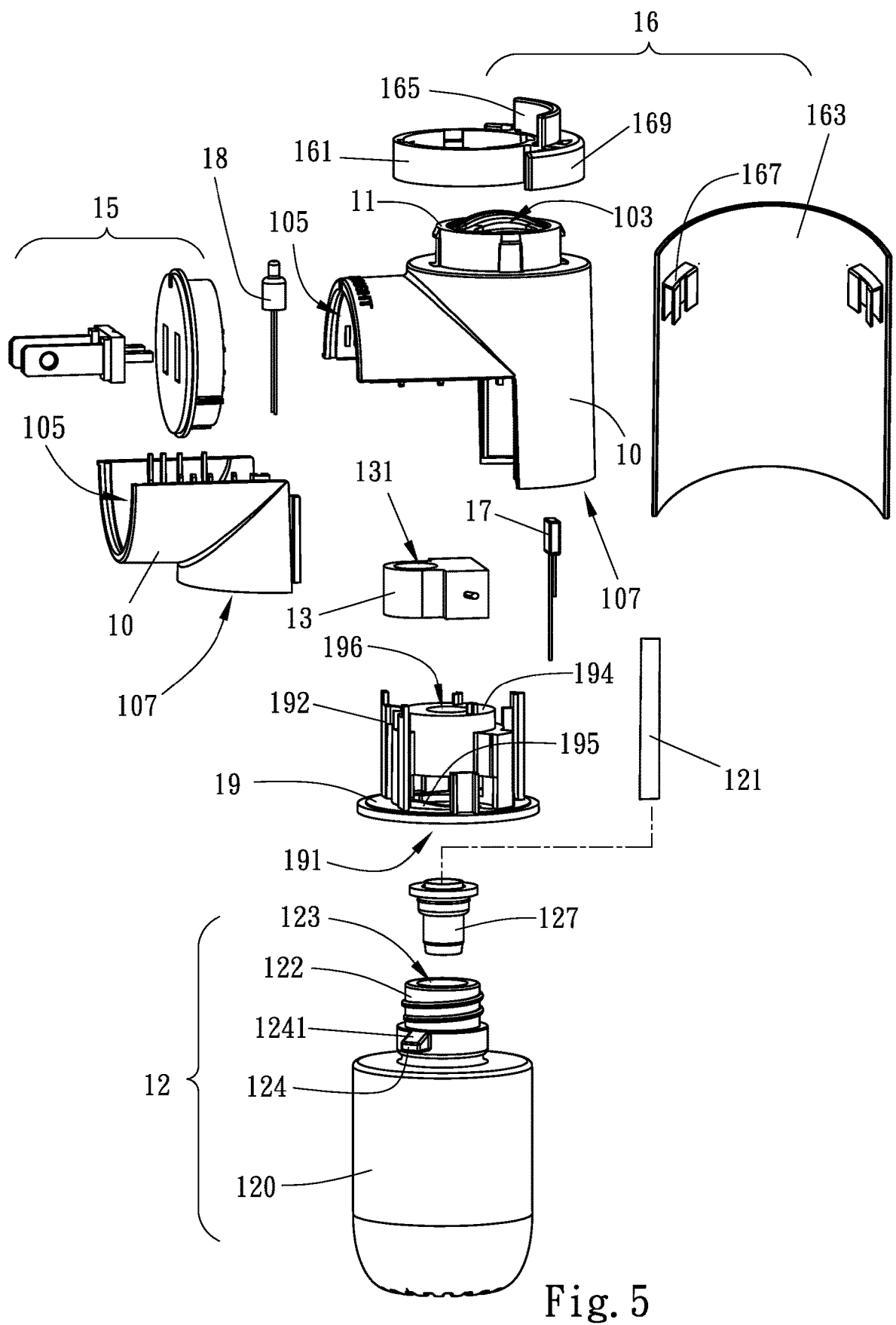
FIG. 5 is an exploded view of an alternate form of the aroma diffuser using a cassette type aroma bottle in accordance with the present invention.
Figure 9:
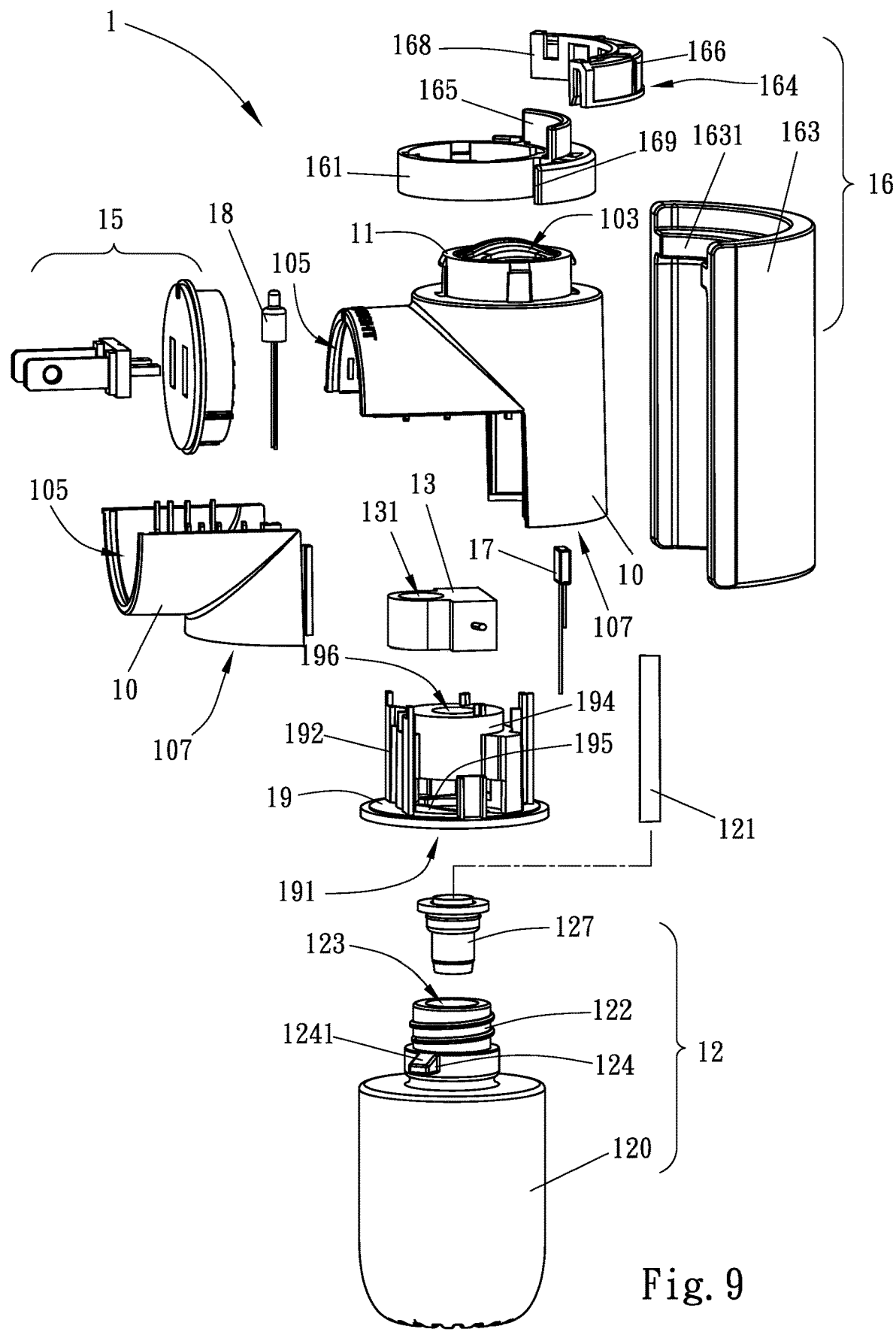
FIG. 9 is an exploded view of another alternate form of the aroma diffuser using a cassette type aroma bottle in accordance with the present invention.

Referring to FIG. 1, FIG. 5 and FIG. 9, the bracket 192 comprises a position-limiting member 194 with a position-limiting hole 196 defined therein. The position-limiting member 194 is inside the bracket 192. The position-limiting member 194 is spaced from the upper side of the circumference of the plug hole 191. The position-limiting hole 196 is formed inside the position-limiting member 194. The position of the position-limiting hole 196 corresponds to the plug hole 191.

Figure 4:
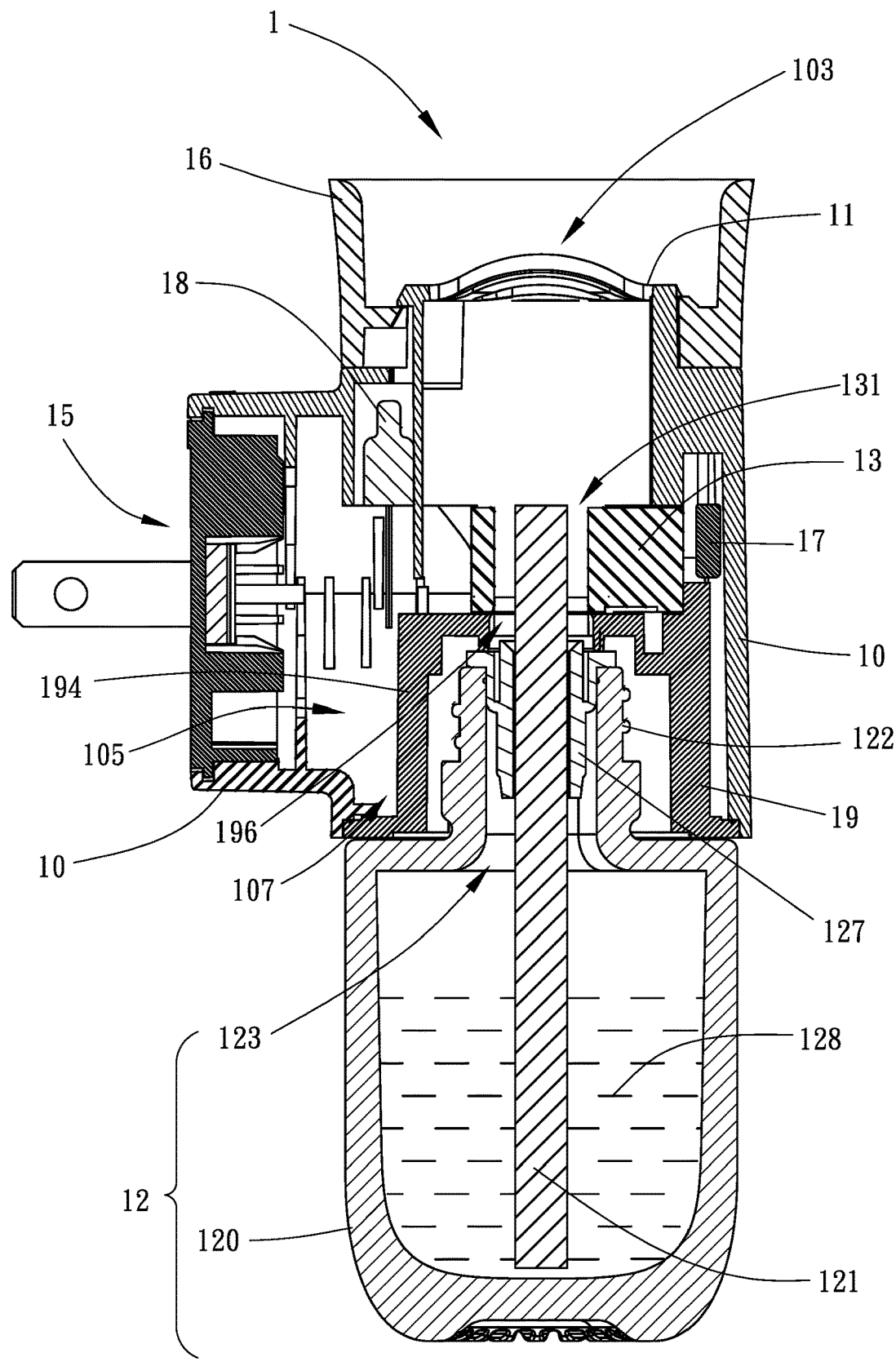
FIG. 4 is a sectional side view of the aroma diffuser shown in FIG. 1.
Figure 8:
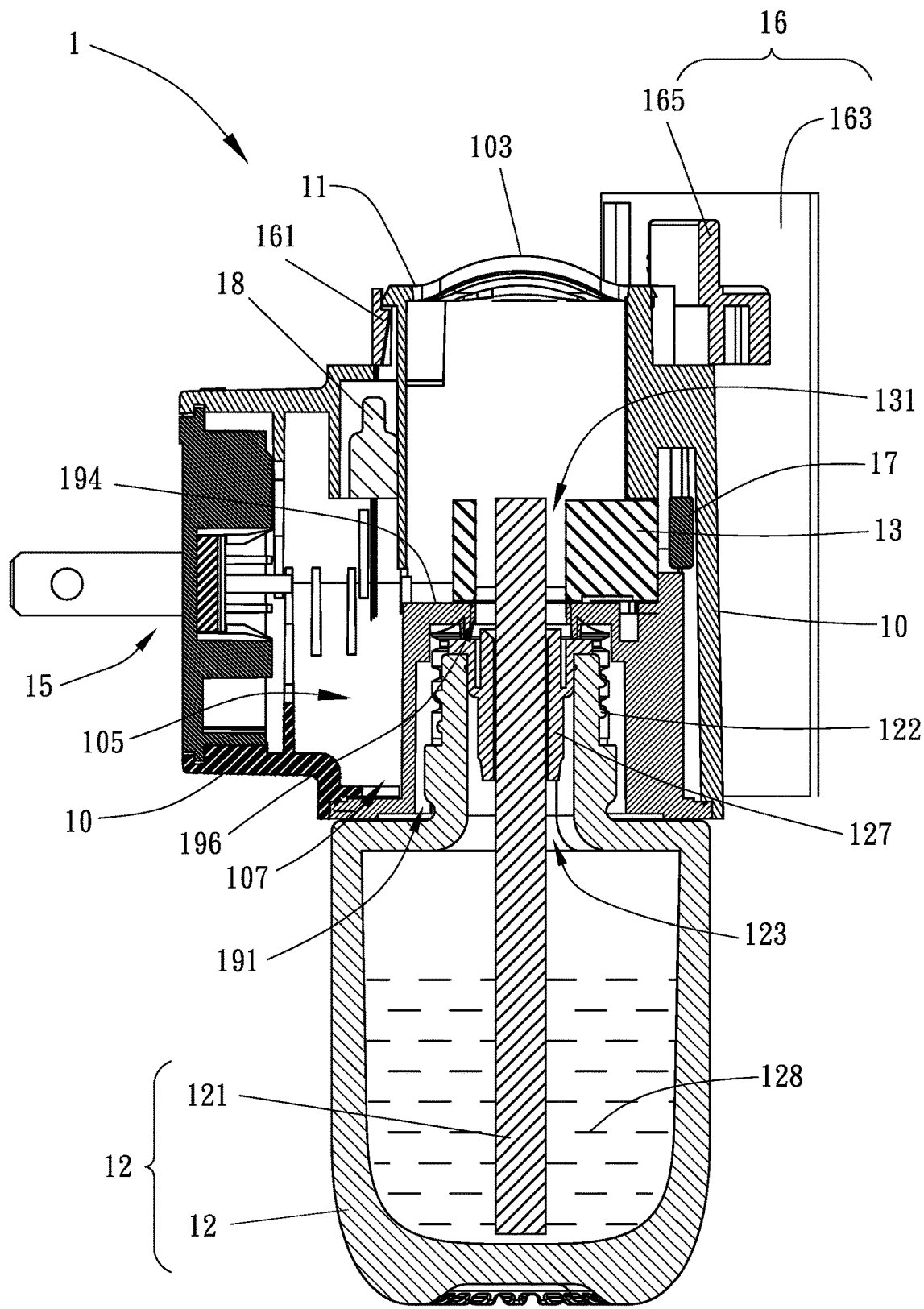
FIG. 8 is a sectional side view of the aroma diffuser shown in FIG. 7.
Figure 12:
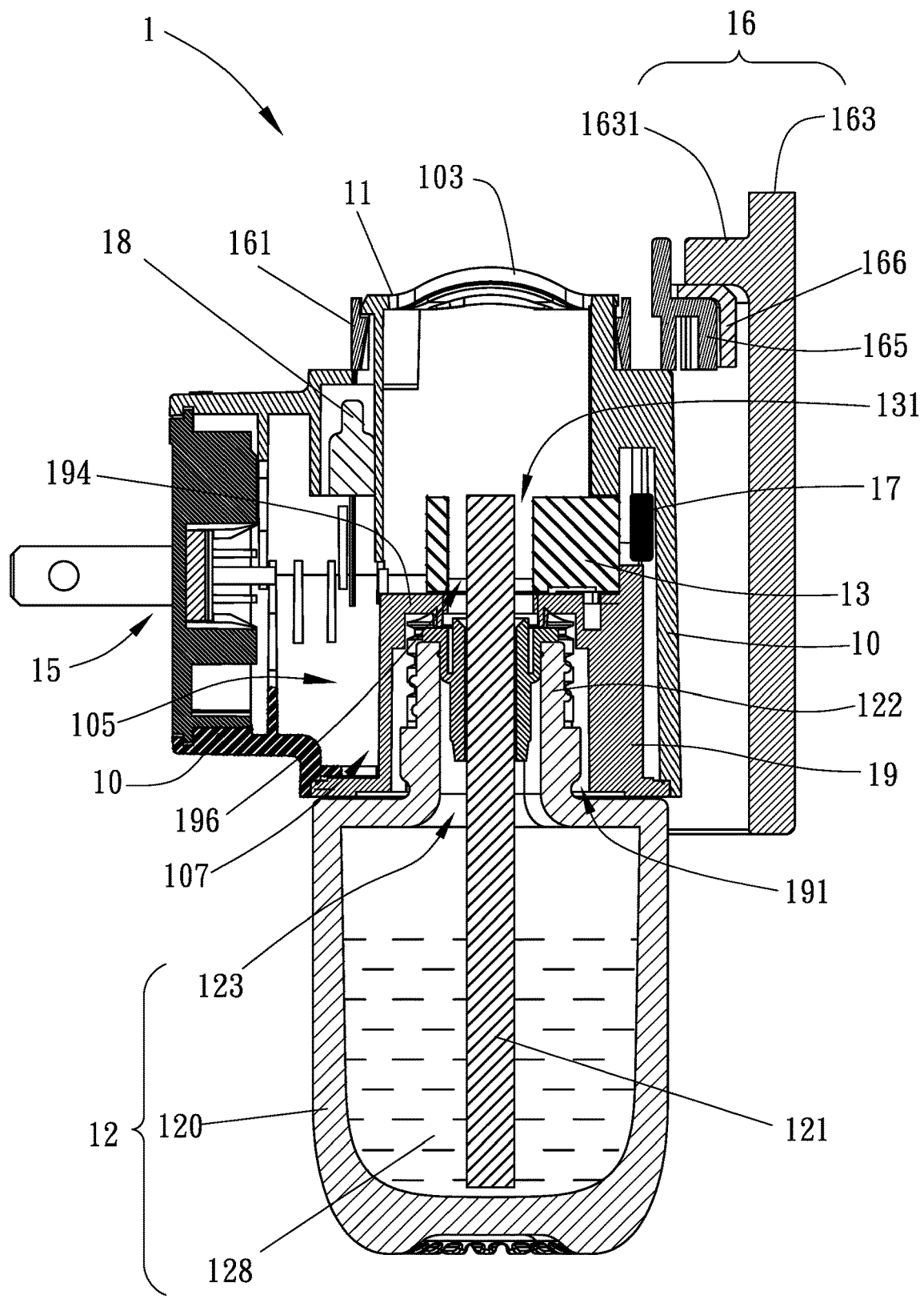
FIG. 12 is a sectional side view of the aroma diffuser shown in FIG. 11.

Referring to FIG. 4, FIG. 8 and FIG. 12, in some embodiments, the upper side of the bracket 192 is used to limit the position of at least one side of the heater 13. The bracket 192 is used to fix the heater 13 inside the bracket 192 to restrict and prevent the heater 13 from being in a predetermined combination position, allowing the heater 13, the position-limiting hole 196 and the plug hole 191 to be quickly combined in the upper and lower corresponding positions of the intended use.

In an embodiment, the position-limiting member 194 includes a cylindrical structure or aa rectangular or other shape, and the position-limiting hole 196 on the inner side thereof may include any structure of a circle, a rectangle, or a triangle.

Referring to FIGS. 1-12, in one embodiment of the present invention, the aroma diffuser 1 using a cassette type aroma bottle further comprises a cassette type aroma bottle 12. The cassette type aroma bottle 12 comprises a bottle body 120, a carrier 121, a neck 122, a bottle opening 123, at least one locating block 124, and an aroma liquid 128. The aroma liquid 128 is filled in the bottle body 120. The neck 122 extends from the upper side of the bottle body 120. The bottle opening 123 is formed at the upper end of the neck 122. The locating block 124 is formed on either side of the surface of the neck 122. The carrier 121 has one side thereof joined to the aroma liquid 128 in the bottle opening 123, and an opposite side thereof extended out of the bottle opening 123. The carrier 121 has capillary pores to absorb the aroma liquid 128. The aroma liquid 128 is continuously absorbed by the capillary of the carrier 121 and transported to the carrier 121 outside the bottle opening 123. The aroma liquid 128, which resides inside the capillary pores of the carrier 121, can contact the air to quickly and efficiently dissipate the aroma molecules. The aroma liquid 128 does not flow over the carrier 121, so the aroma diffuser using a cassette type aroma bottle: is safer to use the aroma bottle. However, some fragrance liquids, such as scented essential oil carriers, do not readily release aroma molecules at room temperature and require heating to release aroma molecules.

On the other hand, the aroma liquid of some fragrances is not very volatile, such as fragrance liquids, essential oils, fragrance oils with water, essences, fragrance oils and other aroma liquids in the carrier is not easy to quickly or massively volatilize to release the aroma at room temperature and needs to be heated to quickly release a large amount of aroma molecules to meet environmental requirements. The cassette type aroma bottle 12 can be quickly and easily detachably engaged in the bottle holder 19 by passing the neck 122 of the cassette type aroma bottle 12 and the free end side of the carrier 121 through the plug hole 191. Since the position-limiting member 194 and the plug hole 191 are separated by a distance from the upper side of the circumference, the locating block 124 can be rotated to the left or right by an angle after passing through the guide groove 193, and the locating block 124 is stuck in the plug hole 191 to secure the cassette type aroma bottle 12 to the bottle holder 19. At the same time, the free end side of the carrier 121 is guided and restricted by the position-limiting member 194 so that the carrier 121 can correctly protrude and be heated by the heater 13 to effectively volatilize the aroma of the aroma liquid.

Referring to FIGS. 1, 5, 9, 13 and 14, the at least one locating block 124 of the cassette type aroma bottle 12 symmetrically matches the number of the at least one guide groove 193. The at least one guide groove 193 or the at least one locating block 124 may be one or more. In the present preferred embodiment, the number of the at least one guide groove 193 and the number of the at least one locating block 124 are symmetrically two.

In some embodiments of the present invention, the aroma bottle 12 can be quickly and detachably engaged in the bottle holder 19 by passing the neck 122 of the cassette type aroma bottle 12 and the free end side of the carrier 121 through the plug hole 191 and then rotating the locating block 124 to the left or right by an angle. Since the position-limiting member 194 and the plug hole 191 are separated by a distance from the upper side of the circumference, the locating block 124 can be rotated to the left or right by an angle after passing through the guide groove 193, and the locating block 124 is stuck in the plug hole 191 to secure the cassette type aroma bottle 12 to the bottle holder 19. At the same time, the free end side of the carrier 121 passes through the position-limiting hole 196. With the limitation of the position-limiting hole 196, the free end side of the carrier 121 will not bend or deviate, and can correctly protrude adjacent to the heater 13, and the carrier 121 will not touch the heater 13. Therefore, the aroma liquid 128 absorbed by the carrier 121 will not stick to the heater 13 for heating, so it can prevent the aroma liquid 128 from sticking or adsorbing on the heater 13, thus avoiding the leakage of the aroma liquid 128 from the heater 13 to the internal of the aroma diffuser of the present invention. The free end side of the carrier 121 that extends out of the bottle opening 123 is disposed adjacent to the heater 13. The electric plug 15 is connected to a power source and electrically connected to the heater 13. The power source supplies power to the heater 13 to generate a heat source. The heat source is transferred to the carrier 121 and conducted to the aroma liquid 128 in the carrier 121. As the temperature increases, the aroma liquid 128 agglomerates the movement of the aromatic molecules, and the collision probability between the molecules becomes larger, resulting in more effective collisions, and the reaction is faster, thereby effectively volatilizing the aroma liquid 128 into fine aromatic molecules from the capillary of the carrier 121, and thus, the volatilized aromatic molecules are dissipated outward to the environment and mixed with air to produce aroma. In contrast, the locating blocks 124 of the cassette type aroma bottle 12 can be rotated to the upper side of the respective guide grooves 193 and moved downwardly through the respective guide grooves 193, allowing the aroma bottle 12 to be separated from the plug hole 191.

In some embodiments of the present invention, the bottle opening 123 of the cassette type aroma bottle 12 is internally engaged with a stopper 127. The stopper 127 is engaged inside the bottle opening 123. The carrier 121 has the free end side thereof passes through the stopper 127. The stopper 127 is used to further fix the carrier 121 at the bottle opening 123, and further prevent the aroma liquid 128 from leaking from the bottle opening 123. Preferably, the stopper 127 is made of an elastic material such as rubber, plastic or silicone rubber.

In the preferred embodiment of the present invention, the aperture of the guide grooves 193 is larger than the volume of the locating blocks 124. While the neck 122 of the cassette type aroma bottle 12 is placed in the plug hole 191, the user can attach the locating blocks 124 to the bottom surface of the bottle holder 19 and then rotate the cassette type aroma bottle 12 to move the locating blocks 124 to the lower side of the respective guide grooves 193. At this moment, the fingers of the user can sense the tactile sensation of the locating blocks 124 touching the respective guide grooves 193, or the user even can hear the auditory sound of the locating blocks 124 colliding with the depressed guide grooves 193. At this time, the user only needs to gently push the cassette type aroma bottle 12 upwards so that the locating blocks 124 can easily fall upward into the respective guide grooves 193 and pass the respective guide grooves 193. Thereafter, the user can use the fingers to rotate the cassette type aroma bottle 12 relative to the bottle holder 19 by an angle to either the left or the right side, so that the cassette type aroma bottle 12 can be engaged in the bottle holder 19 above the plug hole 191. In contrast, the locating blocks 124 of the cassette type aroma bottle 12 can be rotated by an angle to the left or right side to the upper side of the respective guide grooves 193. At this moment, the fingers of the user can sense the tactile sensation of the locating blocks 124 touching the respective guide grooves 193, or the user even can hear the auditory sound of the locating blocks 124 colliding with the depressed guide grooves 193. At this time, the user only needs to gently push the cassette type aroma bottle 12 downwards so that the locating blocks 124 can easily fall downward into the respective guide grooves 193 and pass the respective guide grooves 193, and thus, the cassette type aroma bottle 12 is disengaged from the plug hole 191 of the bottle holder 19. The design of the aroma diffuser using a cassette type aroma bottle: 1 facilitates mounting the cassette type aroma bottle 12 in the plug hole 191 or replacing the cassette type aroma bottle 12. Compared with the threaded mount type aroma bottles of the conventional aroma diffuser designs, the invention is convenient and rapid to use, and the cassette type aroma bottle 12 can be stably assembled in the plug hole 191 without loosening.

Figure 13:
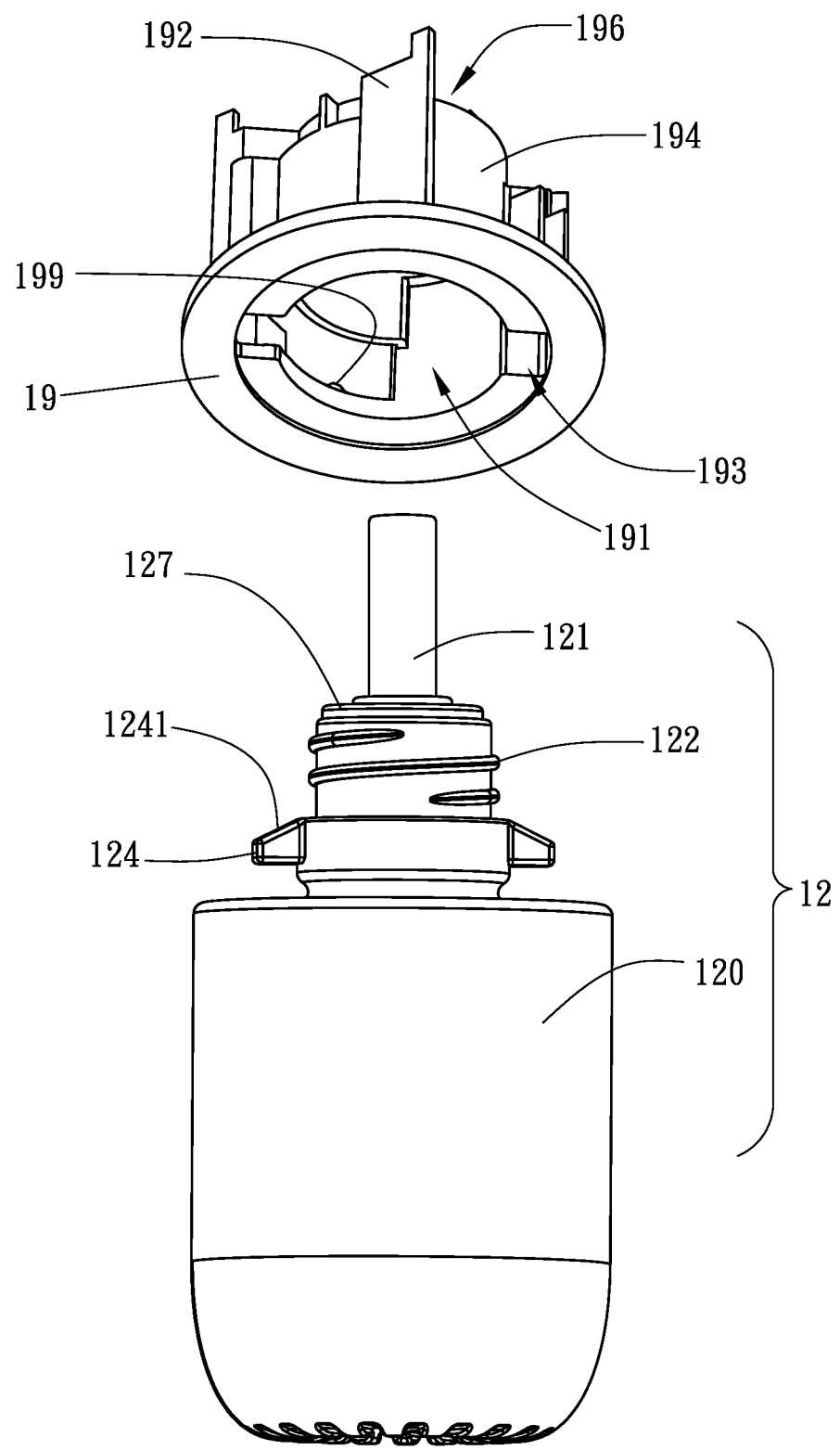
FIG. 13 is an exploded view of the cassette type aroma bottle and the bottle holder of the aroma diffuser in accordance with the present invention.
Figure 14:
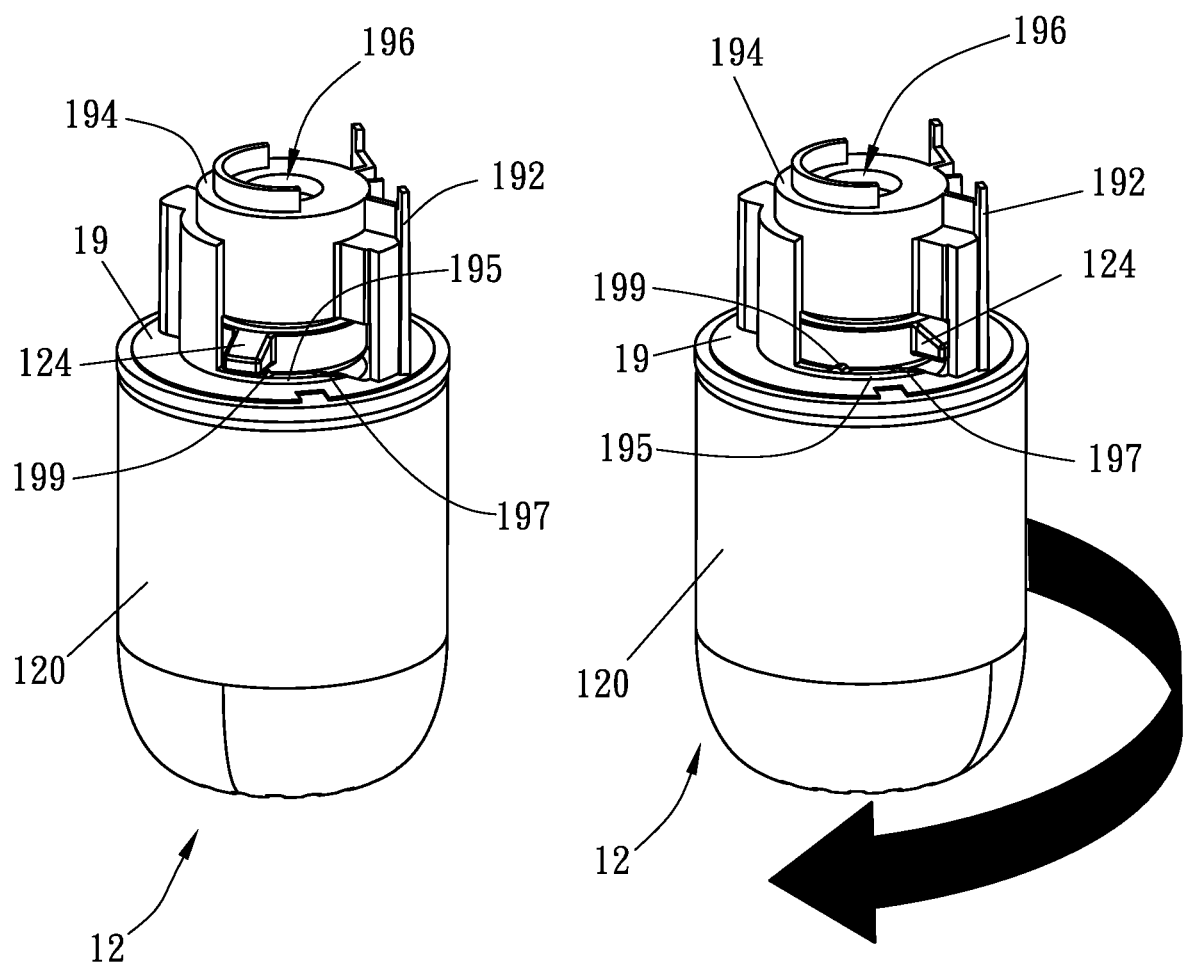
FIG. 14 is a schematic drawing illustrating the assembly procedure of the cassette type aroma bottle and the bottle holder of the aroma diffuser in accordance with the present invention.

Referring to FIGS. 13 and 14, the bottle holder 19 further comprises a locating flange 195 upwardly extended from the periphery of the plug hole 191 and the guide grooves 193 to a predetermined height. The width of the upper edge of the locating flange 195 may be less than the length of the locating blocks 124. Furthermore, the length of the locating blocks 124 is greater than the width of the upper edge of the locating flange 195, and the locating blocks 124 can be smoothly moved along the upper edge of the locating flange 195, facilitating smooth use of the cassette type aroma bottle 12 in the aroma diffuser 1.

In some embodiments of the present invention, the user pushes the neck 122 and locating blocks 124 of the cassette type aroma bottle 12 through the plug hole 191 and the guide grooves 193, and then rotates the cassette type aroma bottle 12 by an angle to force the locating blocks 124 into engagement with the upper side of the locating flange 195. The height formed by the locating flange 195 further presses against the locating blocks 124 and the neck 122 in the plug hole 191, so that the cassette type aroma bottle 12 is completely fixed on the plug hole 191 without shaking. The cassette type aroma bottle 12 is still fixed on the plug hole 191 without shaking even after repeated use for a long time. Compared with the conventional aroma diffuser to secure the aroma bottle by a screw joint that is easy to loosen, the invention uses the plug hole 191 and the guide grooves 193 for the engagement of the locating blocks 124 to firmly secure the cassette type aroma bottle 12 in position without shaking, which overcomes the problem of the conventional products.

In some embodiments of the present invention, the locating flange 195 comprises an inclined surface structure 197. The inclined surface structure 197 is formed by gradually rising a distance from one side of the guide groove 193 to the other. The locating blocks 124 can be rotated (slid) smoothly through the inclined surface structure 197 to the upper side of the locating flange 195 to achieve installation, or rotated away from the upper side of the locating flange 195 through the inclined surface structure 197 to separate from the locating flange 195, forming the quick tactile effect of whether the cassette type aroma bottle 12 is firmly clamped or separated from the plug hole 191, so that the user's hand can tactilely judge the stroke of the cassette type aroma bottle 12 fixed in the aroma diffuser.

In some embodiments of the present invention, the locating flange 195 further comprises a blocking portion 199 formed on one side of the inclined surface structure 197. The blocking portion 199 may be provided with a non-slip rough surface on the upper side thereof. As a result, the locating block 124 slides over the blocking portion 199, and the blocking portion 199 forms a blocking effect for fixing one side of the locating block 124. Conversely, if the user wants to replace the cassette type aroma bottle 12, the user needs to turn the locating block 124 toward the other side and use a force that exceeds the threshold of the blocking portion 199 to allow the locating block 124 to separate from the blocking portion 199. The tactile feel produced by the above operation can let the user know more clearly that the locating blocks 124 of the cassette type aroma bottle 12 is stuck on the locating flange 195, so as to determine the tightness of the locating blocks 124 on the locating flange 195.

Referring to FIGS. 13 and 14, in the preferred embodiment of the present invention, the upper side of the locating block 124 is formed with a slope 1241 which is gradually raised from the free end of the locating block 124 toward the neck 122, so that the locating block 124 can be pushed up into the respective guide groove 193 more smoothly.

Referring to FIGS. 2, 4, 6, 8, 10 and 12, the heater 13 has a heat collection structure 131. The heat collection structure 131 may be formed by opening a hole in the middle of the heater 13. Alternatively, the heat collection structure 131 can be a curved wall extending around the border area of the heater 13. Thus, the inner space of the hole or the curved wall forms a heat collection area. After the user pushed the neck 122 and locating blocks 124 of the cassette type aroma bottle 12 through the plug hole 191 and the guide grooves 193 and rotated the cassette type aroma bottle 12 by an angle to engage locating blocks 124 above the plug hole 191, the cassette type aroma bottle 12 is secured to the bottle holder 19. At this time, the fee end side of the carrier 121 extends through the position-limiting hole 196. With the limitation of the position-limiting hole 196, the free end side of the carrier 121 will not bend or deviate, and can correctly protrude adjacent to the heater 13, and at least a part of the free end side of the carrier 121 is surrounded by the heat collection structure 131, so that the heat source can surround the carrier 121 to evenly heat the carrier 121, thereby enhancing the heating effect of the aroma liquid 128 in the carrier 121. At the same time, the carrier 12 and the adsorbed aroma liquid 12 will not contact the heater 13 to prevent the aroma liquid 12 from being contacted by the heater 13 and seeping into the inside of the aroma diffuser.

Preferably, the heat collection structure 131 shown in the annexed drawings is a cylindrical hole. In the present preferred embodiment, the free end side of the carrier 121 suspends in the cylindrical hole of the heat collection structure 131 so that the carrier 12 and the adsorbed aroma liquid 12 will not contact the heater 13 to prevent the aroma liquid 12 from being contacted by the heater 13 seeping into the inside of the aroma diffuser. And the aroma liquid 128 in the carrier 121 can be efficiently heated to dissipate aromatic molecules.

Referring to FIGS. 1, 4, 5, 9 and 12, the housing 10 further comprises an annular flange 11 and a guide cup 16. The annular flange 11 extends from the border edge of the opening 103 by a height. The guide cup 16 in some embodiments is a tubular shell coupled to the outer wall of the annular flange 11 and disposed in communication with the space inside the annular flange 11. The heat source generated by the heater 1 heats the aroma liquid 128 in the capillary pores of the carrier 121 to dissipate aromatic molecules that pass through the space inside the annular flange 11 and are guided by the guide cup 16 upwardly into the outside air. The guide cup 16 also has the function of decorating the aroma diffuser, and can have different shape combinations to decorate the shape of the aroma diffuser.

Figure 6:
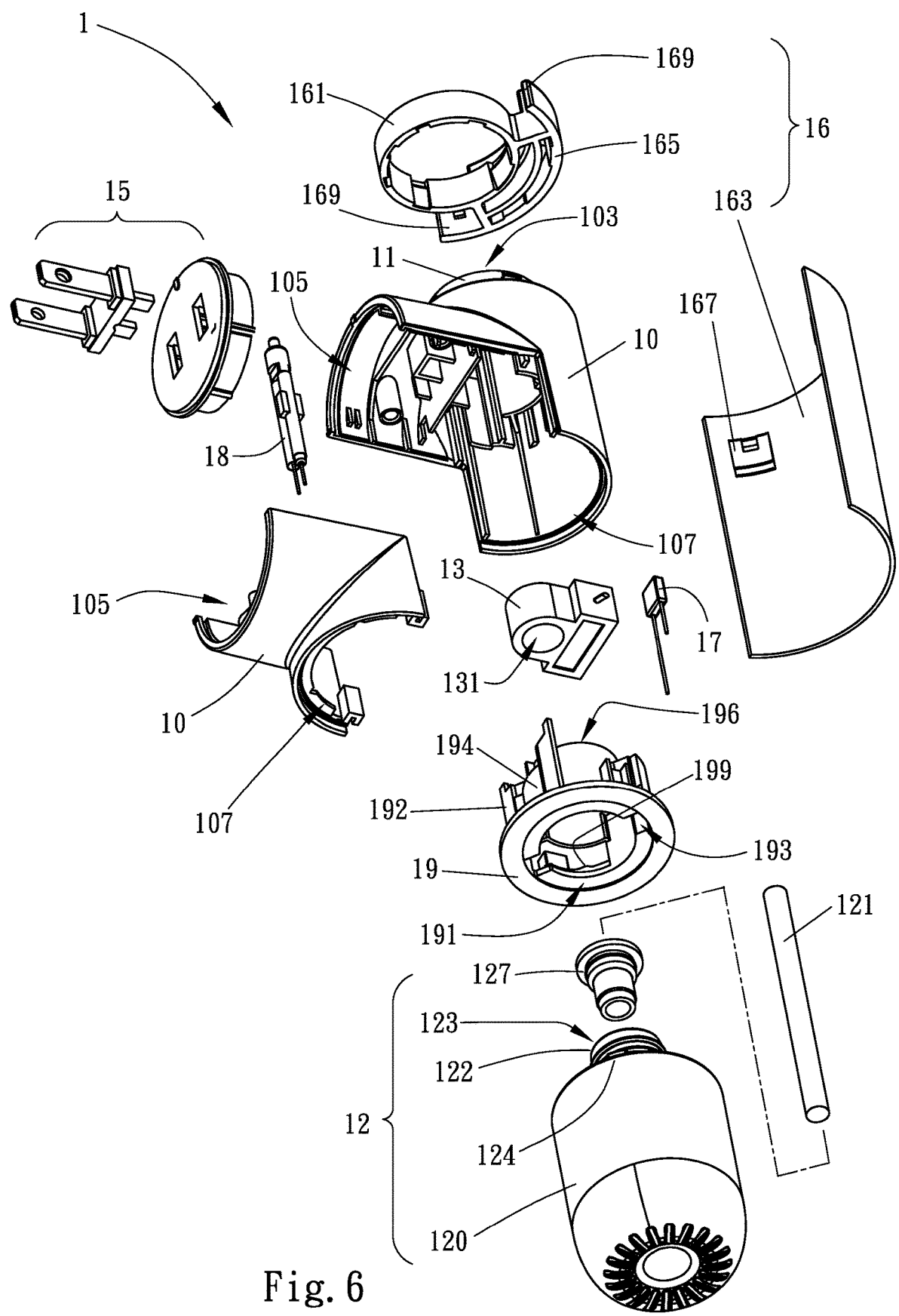
FIG. 6 corresponds to FIG. 5 when viewed from another angle.
Figure 7:
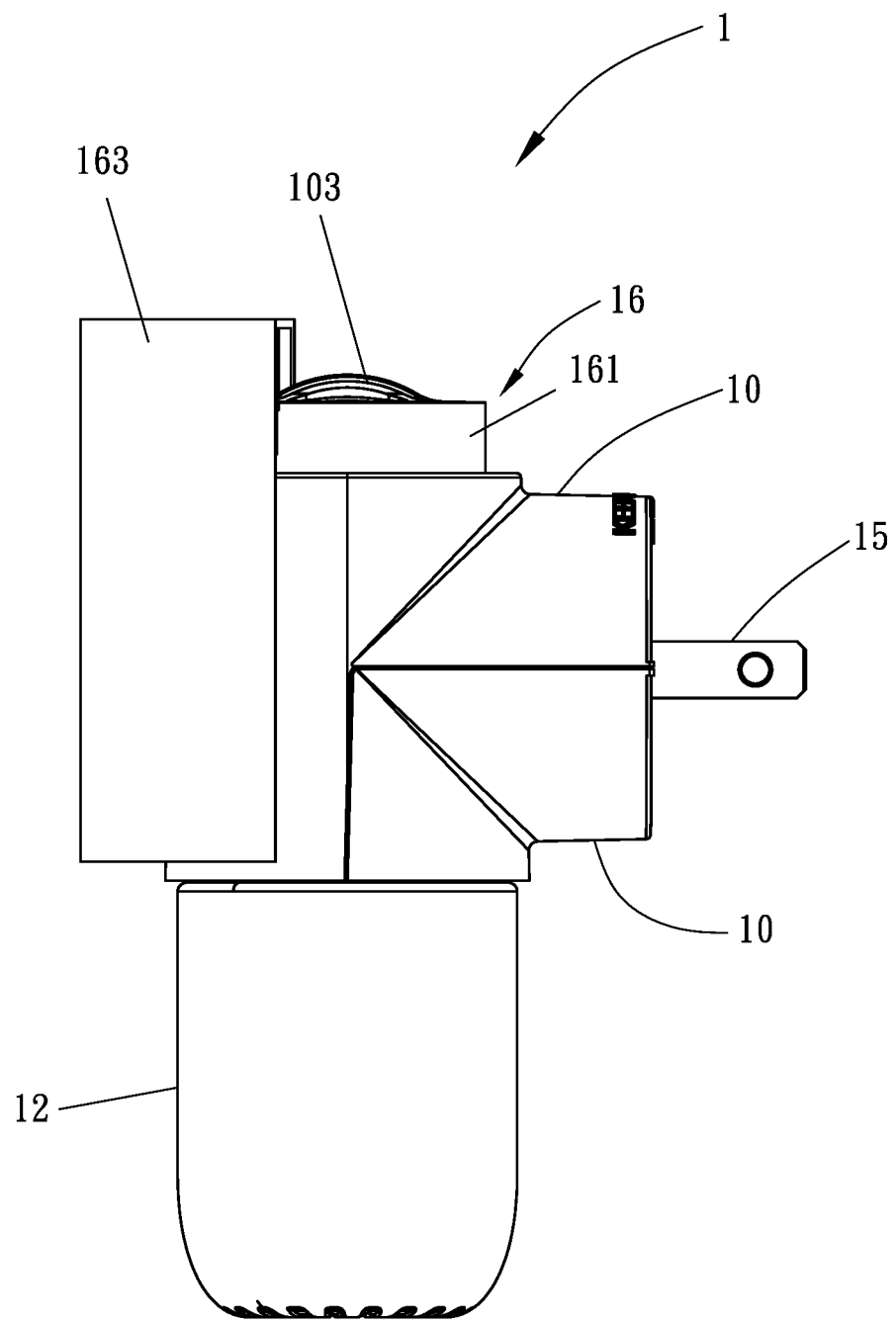
FIG. 7 is a side view of the aroma diffuser shown in FIG. 7.

Referring to FIGS. 5, 6 and 8, in one embodiment of the present invention, the guide cup 16 comprises an annular cup frame 161 and a cover 163. The annular cup frame 161 is combined on the outer side of the annular flange 11. The cover 163 is combined on one side of the annular cup frame 161. In one embodiment, the annular cup frame 161 comprises a hanging member 165 protruding around one side of the annular cup frame 161. The cover 163 is provided with hooks 167 for hooking on the hanging member 165. In the embodiment shown in FIGS. 5, 6 and 8, the hanging member 165 is an arc-shaped belt structure, and the middle side is connected to the periphery of the annular cup frame 161. The hanging member 165 has two free ends 169 formed on both sides of the arc-shaped belt structure. The hooks 167 are formed on the inner wall of the cover 163. By means of hooking the hooks 167 on the free ends 169 of the hanging member 165, the cover 163 is detachably assembled on the outer side of the guide cup 16. In this way, the shape and material of the cover 163 can be changed to provide different decorative configurations. For example, the guide cup 16 or the cover 163 is plastic, metal, ceramic or glass, or various shapes and patterns of transparent or opaque materials, to meet the changing needs of consumers.

Figure 10:
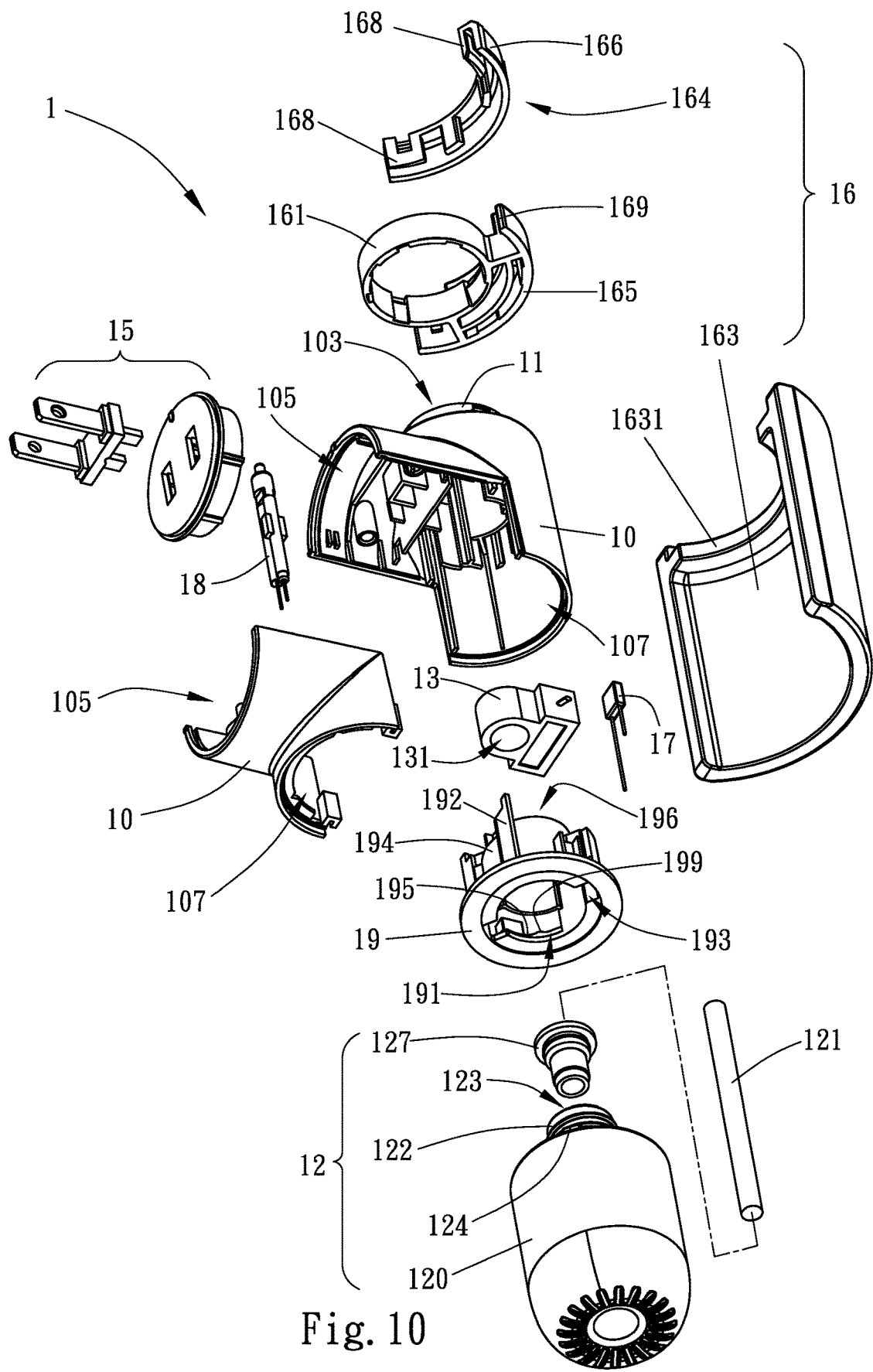
FIG. 10 corresponds to FIG. 9 when viewed from another angle.
Figure 11:
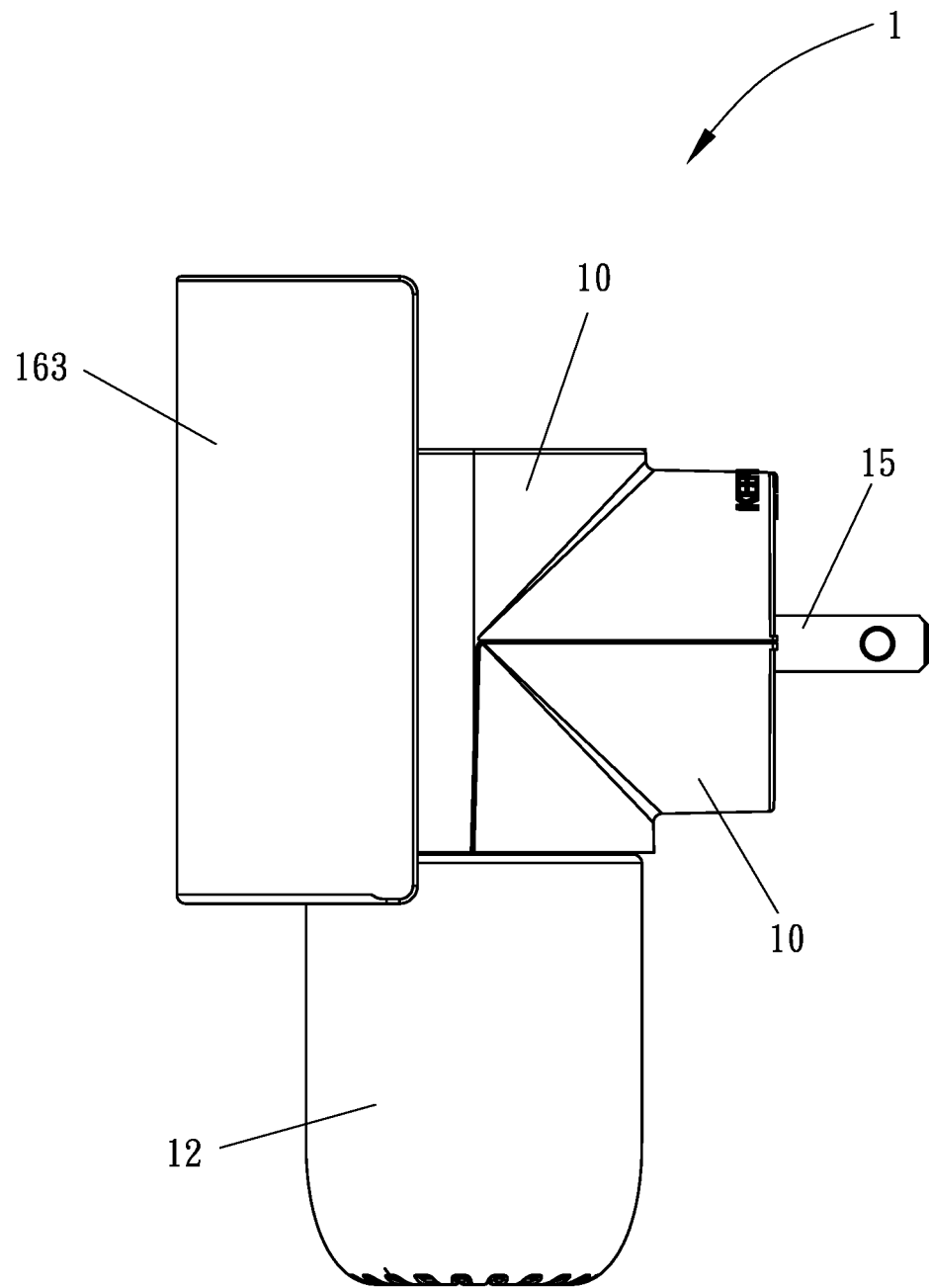
FIG. 11 is a side view of the aroma diffuser shown in FIG. 9.

Referring to FIGS. 9, 10 and 12, in one embodiment of the present invention, the guide cup 16 further comprises a fixing member 164, which is different from the above-mentioned embodiment in that the fixing member 164 can be used to connect a cover 163 that has no ductility of plasticity. For example, the cover 163 is made of ceramic, stone or glass, which is difficult to make various hooks for hanging on the hanging member of the annular cup frame 161. Therefore, in the drawings of this embodiment, the fixing member has a double-layer arc-like structure. The outer layer of the double-layer arc-like structure is an arc wall 166, and the inner layer of the double-layer arc-like structure provides a plurality of hooked portions 168. By means of hooking the hooked portions 168 on the free ends 169 of the hanging member 165 of the annular cup frame 161, the fixing member 164 is combined to the annular cup frame 161. The cover 163 made of ceramic, stone or glass, etc. includes a protrusion 1631. The protrusion 1631 is fastened to the outer side of the fixing member 164 by adhesive bonding or screw locking or clamping methods.

Referring to FIGS. 1, 2, 4-6, 8-10 and 12, in one embodiment of the present invention, the aroma diffuser further comprises a fuse device 17 electrically connected between the heater 13 and the power line (not shown) of the aroma diffuser. The fuse device 17 is mounted inside the housing 10 to detect the temperature of the heater 13. The fuse device 17 is preset with a temperature threshold, such as 110° C., 105° C., and other preset temperatures. If the accumulated temperature of the heater 13 in use of the aroma diffuser reaches the threshold, the fuse device 17 will disconnect the power supply and turn off the heater 13.

Referring to FIGS. 2-6, in one embodiment of the present invention, the aroma diffuser further comprises a light source 18 electrically connected to the power line of the aroma diffuser. The power line electrically connects the power source to the heater 13 and the light source 18. The light signal of the light source 18 shows that the aroma diffuser is turned on and the heater 13 generates a heat source to heat the aroma liquid inside the carrier 121, and the light can penetrate the housing 10 to provide the light decoration or night light source effect of the aroma diffuser.

In some embodiments of the present invention, the carrier 121 can be any of a variety of absorbers that can absorb the aroma liquid 128, store the aroma liquid 128 and prevent the aroma liquid 128 from flowing. The carrier 121 can be heated to transfer the heated temperature to the aroma liquid 128 in the capillary pores thereof, causing the aroma liquid 128 to be volatilized and diffused through the air. The carrier 121 can be a fiber bundle, a porous plastic material, such as porous PE plastic product, a porous ceramic, a porous gypsum product, or a suction core (cotton, foam, cloth).

Figure 15:
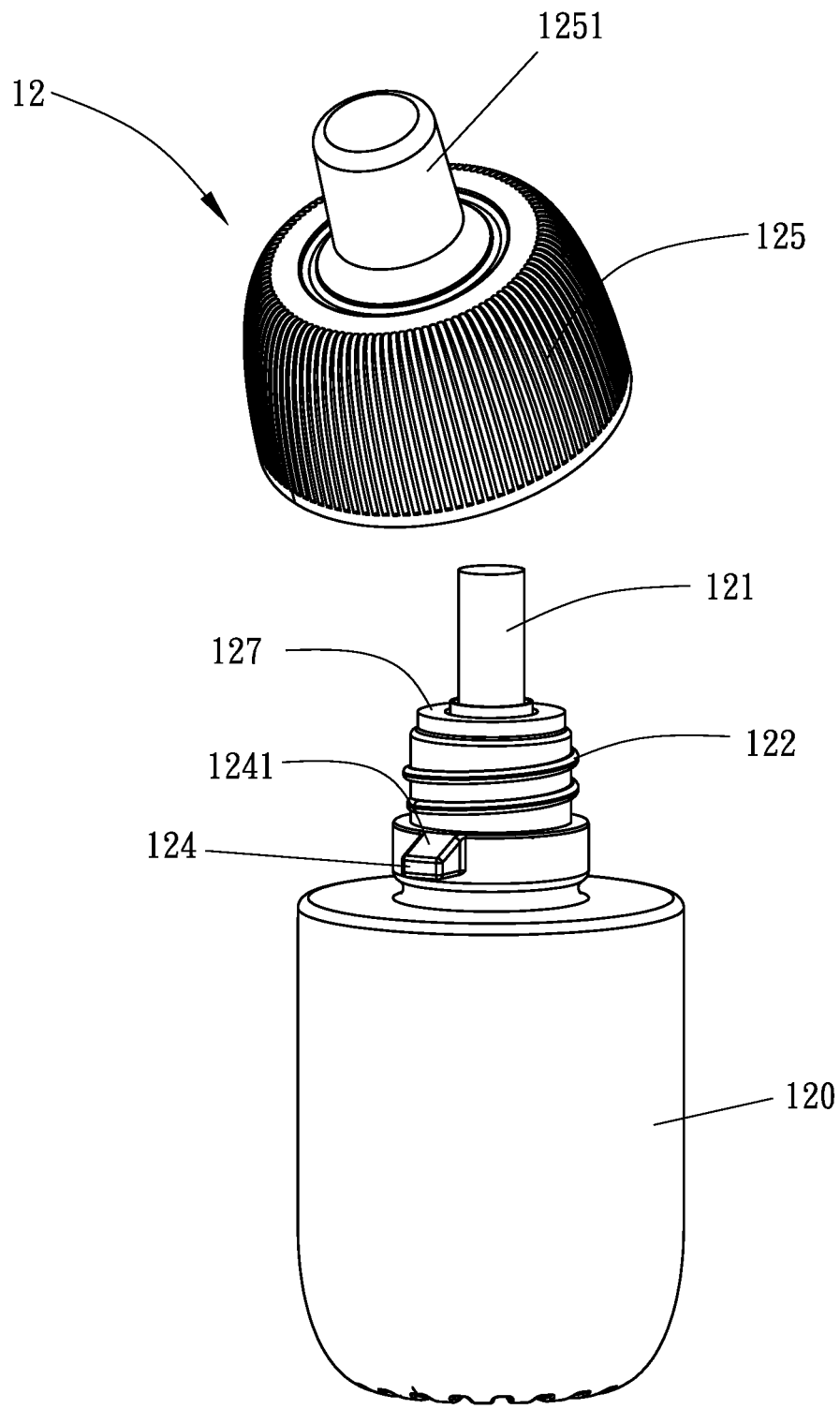
FIG. 15 is an exploded view of the cassette type aroma bottle and the bottle cap of the aroma diffuser in accordance with the present invention.

Referring to FIG. 15, in one embodiment of the present invention, the cassette type aroma bottle 12 further comprises a bottle cap 125. The bottle cap 125 comprises a hollow protective tube 1251 formed by protruding a height from the upper side of the body of the bottle cap 125. The bottle cap 125 is used to bind to the neck 122 of the cassette type aroma bottle 12 and to surround the free end side of the carrier 121. The hollow protective tube 1251 is used to protect the carrier 121, thereby keeping the free end side of the carrier 121 outside the bottle body 120 from being bent and deformed during storage and transportation and preventing the aroma liquid 128 inside the carrier 121 from volatilizing.

Although particular embodiments of the present invention have been described in detail for purposes of illustration, various modifications and enhancements may be made without departing from the spirit and scope of the invention. Accordingly, the invention is not to be limited except as by the appended claims.

What the invention claimed is:

1. An aroma diffuser using an aroma bottle, comprising:
a housing comprising an opening, a first hole and a second hole, said opening being located on one lateral side of said housing, said second hole being located on an opposite lateral side of said housing, said first hole being disposed between said opening and said second hole;
a heater mounted inside said housing;
an electric plug mounted in said first hole of said housing and electrically connected with said heater; and
a bottle holder mounted in said second hole, said bottle holder comprising a plug hole formed in a bottom side thereof, at least one guide groove respectively recessed from the periphery of said plug hole, and a bracket formed on an upper peripheral edge of said plug hole,
wherein said bottle holder further comprises a locating flange upwardly extended from the periphery of said plug hole and said guide grooves to a predetermined height;
wherein said locating flange comprises an inclined surface structure;
wherein said locating flange further comprises a blocking portion formed on one side of said inclined surface structure, said blocking portion being provided with a non-slip rough surface on an upper side thereof.

2. The aroma diffuser as claimed in claim 1, wherein said bracket comprises a position-limiting member with a position-limiting hole defined therein, said position-limiting member being disposed inside said bracket, said position-limiting member being spaced from an upper side of the circumference of said plug hole, said position-limiting hole being formed inside said position-limiting member corresponding to said plug hole.

3. The aroma diffuser as claimed in claim 2, wherein said bracket has an upper side thereof used to limit the position of at least one side of said heater, said bracket being used to fix said heater therein to restrict and prevent said heater from being in a predetermined combination position, allowing said heater, said position-limiting hole and said plug hole to be combined in the upper and lower corresponding positions of the intended use.

4. The aroma diffuser as claimed in claim 1, wherein said housing further comprises an annular flange extended from the border of said opening to a predetermined height, and a guide cup fastened to the periphery of said annular flange.

5. An aroma diffuser using an aroma bottle, comprising:
a housing comprising an opening, a first hole and a second hole, said opening being located on one lateral side of said housing, said second hole being located on an opposite lateral side of said housing, said first hole being disposed between said opening and said second hole;
a heater mounted inside said housing;
an electric plug mounted in said first hole of said housing and electrically connected with said heater; and
a bottle holder mounted in said second hole, said bottle holder comprising a plug hole formed in a bottom side thereof, at least one guide groove respectively recessed from the periphery of said plug hole, and a bracket formed on an upper peripheral edge of said plug hole,
wherein said housing further comprises an annular flange extended from the border of said opening to a predetermined height, and a guide cup fastened to the periphery of said annular flange;
wherein said guide cup guide cup comprises an annular cup frame and a cover, said annular cup frame being combined on an outer side of said annular flange, said cover being combined on one side of said annular cup frame, said annular cup frame comprising a hanging member protruding around one side thereof, said cover being provided with hooks for hooking on said hanging member.

6. The aroma diffuser as claimed in claim 5, wherein said hanging member is an arc-shaped belt structure, said arc-shaped belt structure having a middle part thereof connected to the periphery of said annular cup frame and two free ends formed on two opposite sides thereof; said hooks are formed on an inner wall of said cover for hooking said free ends of said hanging member.

7. An aroma diffuser using an aroma bottle, comprising:
a housing comprising an opening, a first hole and a second hole, said opening being located on one lateral side of said housing, said second hole being located on an opposite lateral side of said housing, said first hole being disposed between said opening and said second hole;

a heater mounted inside said housing;

an electric plug mounted in said first hole of said housing and electrically connected with said heater; and a bottle holder mounted in said second hole, said bottle holder comprising a plug hole formed in a bottom side thereof, at least one guide groove respectively recessed from the periphery of said plug hole, and a bracket formed on an upper peripheral edge of said plug hole, wherein said housing further comprises an annular flange extended from the border of said opening to a predetermined height, and a guide cup fastened to the periphery of said annular flange;

wherein said guide cup comprises an annular cup frame, a fixing member and a cover, said annular cup frame being combined on an outer side of said annular flange, said fixing member being mounted on said cover and fastened to said annular cup frame, said annular cup frame comprising a hanging member protruding around one side thereof, said hanging member being an arc-shaped belt structure, said arc-shaped belt structure having a middle part thereof connected to the periphery of said annular cup frame and two free ends formed on two opposite sides thereof, said fixing member being a double-layer arc-like structure, said double-layer arc-like structure comprising an outer layer in the form of an arc wall and an inner layer providing a plurality of hooked portions for hooking on said free ends of said hanging member of said annular cup frame, said cover comprising a protrusion fastened to an outer side of said fixing member.

8. The aroma diffuser as claimed in claim 1, further comprising a light source electrically connected to said electric plug and adapted to emit light through said housing for visual decoration and illumination.

9. The aroma diffuser as claimed in claim 1, wherein said heater further comprises a heat collection structure formed of a hole in a middle part of said heater or a curved wall extended along one side of said heater with a heat collection area defined therein.

10. The aroma diffuser as claimed in claim 9, further comprising a cassette type aroma bottle detachably connected to said bottle holder, said cassette type aroma bottle comprising a bottle body, a carrier, a neck, a bottle opening, at least one locating block and an aroma liquid, said aroma liquid being filled in said bottle body, said neck being upwardly extended from an upper side of said bottle body, said bottle opening being formed in a top side of said neck, each said locating block being extended from the periphery of said neck, said carrier having one side thereof mounted in said bottle opening and disposed in contact with said aroma liquid and an opposite side thereof extended out of said bottle opening.

11. The aroma diffuser as claimed in claim 1, further comprising a cassette type aroma bottle detachably connected to said bottle holder, said cassette type aroma bottle comprising a bottle body, a carrier, a neck, a bottle opening, at least one locating block and an aroma liquid, said aroma liquid being filled in said bottle body, said neck being upwardly extended from an upper side of said bottle body, said bottle opening being formed in a top side of said neck, each said locating block being extended from the periphery of said neck, said carrier having one side thereof mounted in said bottle opening and disposed in contact with said aroma liquid and an opposite side thereof extended out of said bottle opening.

12. The aroma diffuser as claimed in claim 2, further comprising a cassette type aroma bottle detachably connected to said bottle holder, said cassette type aroma bottle comprising a bottle body, a carrier, a neck, a bottle opening, at least one locating block and an aroma liquid, said aroma liquid being filled in said bottle body, said neck being upwardly extended from an upper side of said bottle body, said bottle opening being formed in a top side of said neck, each said locating block being extended from the periphery of said neck, said carrier having one side thereof mounted in said bottle opening and disposed in contact with said aroma liquid and an opposite side thereof extended out of said bottle opening.

13. The aroma diffuser as claimed in claim 12, wherein each said locating block has a slope formed on a top side thereof, said slope extending upwardly from the free end of the associated said locating block toward said neck.

14. The aroma diffuser as claimed in claim 13, wherein said bottle opening of said cassette type aroma bottle is internally engaged with a stopper, said stopper being engaged inside said bottle opening and used to fix said carrier in said bottle opening; said carrier has one side thereof passing through said stopper.

15. The aroma diffuser as claimed in claim 14, wherein said cassette type aroma bottle further comprises a bottle cap, said bottle cap comprising a hollow protective tube formed by protruding a height from an upper side of said bottle cap, said bottle cap being used to bind to said neck of said cassette type aroma bottle and to surround said carrier.

* * * * *